United States Patent
Yang et al.

(10) Patent No.: US 10,667,713 B2
(45) Date of Patent: *Jun. 2, 2020

(54) R-R INTERVAL MEASUREMENT USING MULTI-RATE ECG PROCESSING

(71) Applicant: VITAL Connect, Inc., San Jose, CA (US)

(72) Inventors: Yun Yang, Los Altos, CA (US); Ravi Narasimhan, Sunnyvale, CA (US); Nima Ferdosi, San Jose, CA (US)

(73) Assignee: Vital Connect, Inc., San Jose, CA (US)

( * ) Notice: Subject to any disclaimer, the term of this patent is extended or adjusted under 35 U.S.C. 154(b) by 251 days.

This patent is subject to a terminal disclaimer.

(21) Appl. No.: 15/806,673

(22) Filed: Nov. 8, 2017

(65) Prior Publication Data

US 2018/0064361 A1 Mar. 8, 2018

Related U.S. Application Data

(63) Continuation of application No. 13/607,160, filed on Sep. 7, 2012, now Pat. No. 9,814,405.

(51) Int. Cl.
*A61B 5/0456* (2006.01)
*A61B 5/00* (2006.01)
*A61B 5/04* (2006.01)

(52) U.S. Cl.
CPC .......... *A61B 5/0456* (2013.01); *A61B 5/7232* (2013.01); *A61B 5/0006* (2013.01); *A61B 5/04017* (2013.01); *A61B 2560/0209* (2013.01)

(58) Field of Classification Search
CPC ..... A61B 5/486; A61B 5/7275; A61B 5/7282; A61B 5/0402; A61B 5/0456;
(Continued)

(56) References Cited

U.S. PATENT DOCUMENTS

| 5,355,891 A | 10/1994 | Wateridge et al. |
| 9,814,405 B2 * | 11/2017 | Yang .................... A61B 5/0456 |

(Continued)

FOREIGN PATENT DOCUMENTS

| GB | 2067767 A | 7/1981 |
| JP | 08-336502 | 12/1996 |

(Continued)

OTHER PUBLICATIONS

The International Search Report and the Written Opinion of the International Searching Authority for International Application No. PCT/US2013/058258, dated Dec. 13, 2013.

*Primary Examiner* — Deborah L Malamud
(74) *Attorney, Agent, or Firm* — Brundidge & Stanger, P.C.

(57) ABSTRACT

A method and system for R-R interval measurement of a user are disclosed. In a first aspect, the method comprises detecting an electrocardiogram (ECG) signal of the user. The method includes performing QRS peak detection on the ECG signal to obtain a low resolution peak and searching near the low resolution peak for a high resolution peak. The method includes calculating the R-R interval measurement based upon the high resolution peak. In a second aspect, a wireless sensor device comprises a processor and a memory device coupled to the processor, wherein the memory device includes an application that, when executed by the processor, causes the processor to carry out the steps of the method.

11 Claims, 6 Drawing Sheets

(58) Field of Classification Search
CPC .......... A61B 5/0245; A61B 2560/0209; A61B 5/0006; A61B 5/0452; A61B 5/7225; A61B 5/7232; A61B 5/04017; A61B 5/7285; A61N 1/3702
See application file for complete search history.

(56) References Cited

U.S. PATENT DOCUMENTS

| | | |
|---|---|---|
| 2007/0260151 A1 | 11/2007 | Clifford |
| 2011/0066053 A1 | 3/2011 | Yazicioglu |
| 2012/0123232 A1 | 5/2012 | Najarian et al. |

FOREIGN PATENT DOCUMENTS

| | | |
|---|---|---|
| JP | 2001-204714 | 7/2001 |
| JP | 2005-118193 | 5/2005 |
| JP | 2010-094236 | 4/2010 |
| JP | 2010140746 A1 | 12/2010 |
| WO | 2006091636 A2 | 8/2006 |
| WO | WO 2007/103835 | 9/2007 |

* cited by examiner

R-R INTERVAL MEASUREMENT USING MULTI-RATE ECG PROCESSING

This application is a Continuation of U.S. patent application Ser. No. 13/607,160, filed Sep. 7, 2012, which is incorporated herein by reference in its entirety.

FIELD OF THE INVENTION

The present invention relates to wireless sensor devices, and more particularly, to wireless sensor devices that measure R-R intervals using multi-rate ECG processing.

BACKGROUND

Wireless sensor devices are used in a variety of applications including the heart function measurements of users. In many of these applications, a wireless sensor device is attached directly to the user's skin to measure certain data. By combining this measured data with various low complexity heart function measurement algorithms, the heart function measurements of the user are calculated by the wireless sensor device. Imperfections typical to wearable sensor environments include motion artifact noise and baseline wander that degrade the performance of such algorithms.

As a result, extra processing is required to create robust heart function measurement algorithms. Such processing requires extensive mathematical calculations which translate into higher power consumption by the microprocessor of the wireless sensor device. Therefore, there is a strong need for a power efficient solution that utilizes the advantages of robust heart function measurement algorithms while minimizing the power consumption required for the execution of these algorithms. The present invention addresses such a need.

SUMMARY OF THE INVENTION

A method and system for R-R interval measurement of a user are disclosed. In a first aspect, the method comprises detecting an electrocardiogram (ECG) signal of the user. The method includes performing QRS peak detection on the ECG signal to obtain a low resolution peak and searching near the low resolution peak for a high resolution peak. The method includes calculating the R-R interval measurement based upon the high resolution peak.

In a second aspect, a wireless sensor device comprises a processor and a memory device coupled to the processor, wherein the memory device includes an application that, when executed by the processor, causes the processor to detect an electrocardiogram (ECG) signal of the user. The application, when executed by the processor, further causes the processor to perform QRS peak detection on the ECG signal to obtain a low resolution peak, to search near the low resolution peak for a high resolution peak, and to calculate the R-R interval measurement based upon the high resolution peak.

BRIEF DESCRIPTION OF THE DRAWINGS

The accompanying figures illustrate several embodiments of the invention and, together with the description, serve to explain the principles of the invention. One of ordinary skill in the art readily recognizes that the particular embodiments illustrated in the figures are merely exemplary, and are not intended to limit the scope of the present invention.

DETAILED DESCRIPTION

Figure 1:
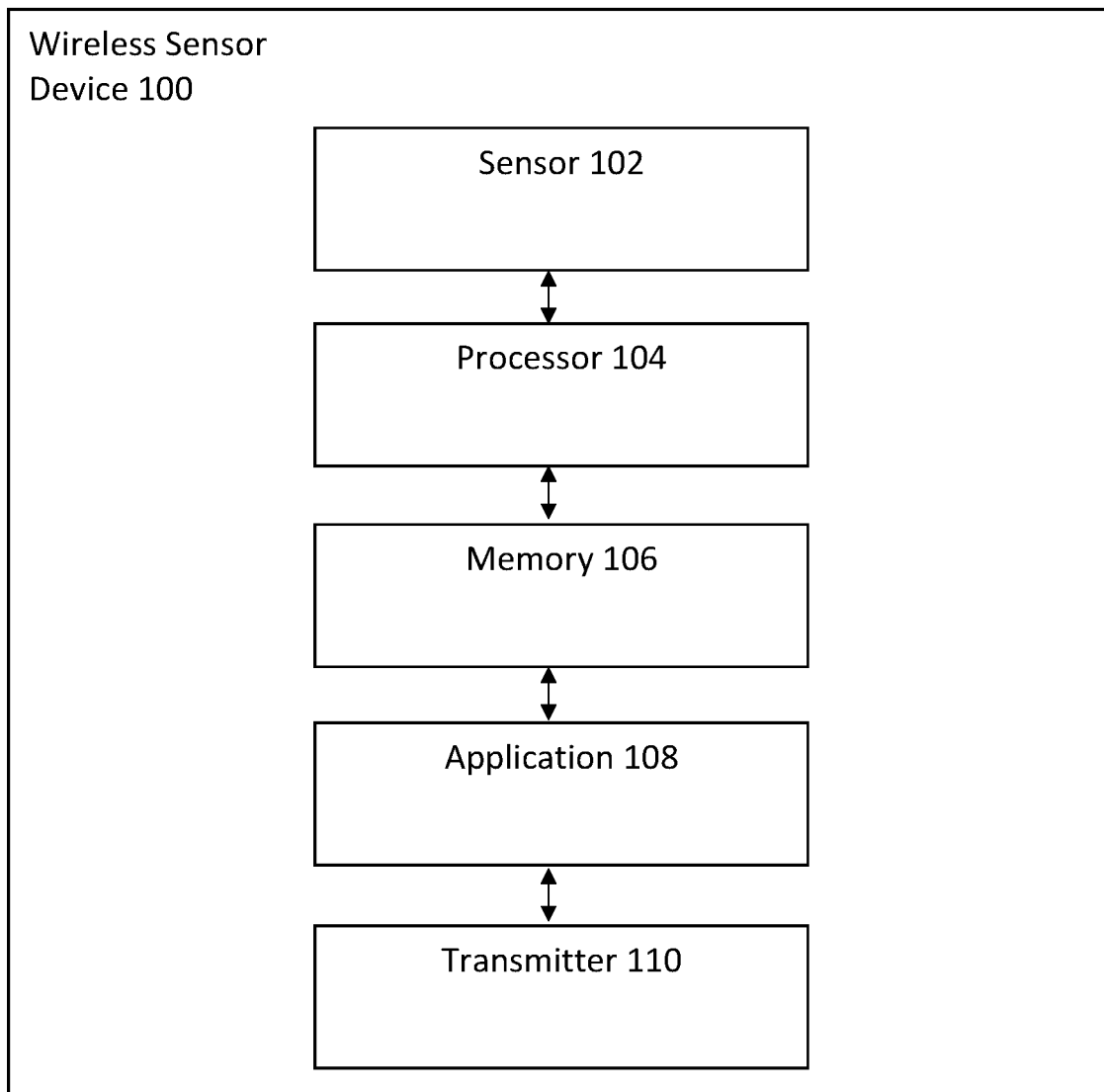
FIG. 1 illustrates a wireless sensor device in accordance with an embodiment.

The present invention relates to wireless sensor devices, and more particularly, to wireless sensor devices that measure R-R intervals using multi-rate electrocardiogram (ECG) processing. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

An R-R interval calculation denotes the time elapsing between two consecutive R waves in an electrocardiogram (ECG). In order to measure an R-R interval based on an ECG of a user, electrodes of a wireless sensor device are attached to the user's body to detect an ECG signal. The signal is then converted from the analog domain to the digital domain using an analog-to-digital converter (ADC). The accuracy of the R-R interval measurement depends on the fidelity of the digital versions of the ECG signal to its original analog version. Higher sampling rates of the ECG signal result in a more accurate R-R interval measurement but also reduce battery life due to the increased power consumption that results from the wireless sensor device computing additional mathematical operations per unit time.

Various low complexity heart function measurement algorithms, including but not limited to Qualified Peak Detection, are computationally simple and achieve adequate performance under optimal conditions and relatively low sampling rates. With these algorithms, the ECG signal is passed through a band-pass filter to remove the baseline and band noise. Local maximums of the ECG signal are found over predetermined time periods. For a local maximum to quality as a QRS peak, the identified local maximum must be higher than a certain peak threshold which helps reject peaks that result from noise or a T wave complex. One of ordinary skill in the art readily recognizes that the peak threshold can be a variety of thresholds including but not limited to a threshold that is a function of the average of previously detected peaks to enable the algorithm to adapt to changes in the ECG signal and that would be within the spirit and scope of the present invention.

A method and system in accordance with the present invention provides robust, low power R-R interval measurement using multi-rate ECG processing. By attaching a wireless sensor device that includes at least one electrode to the user and detecting an ECG signal, high resolution peak detection is achieved either by sampling the analog ECG signal at a higher sampling rate than is needed by a robust DSP peak detection algorithm or by re-sampling the digital ECG signal around a low resolution peak that has been detected by the robust DSP peak detection algorithm. The detected high resolution peak is utilized to calculate the user's R-R interval measurement to arrive at a variety of heart function measurements including but not limited to heart rate and heart rate variability measurements.

One of ordinary skill in the art readily recognizes that a variety of wireless sensor devices can be utilized including but not limited to tri-axial accelerometers, uni-axial accelerometers, bi-axial accelerometers, gyroscopes, electrode systems, and pressure sensors and that would be within the spirit and scope of the present invention.

To describe the features of the present invention in more detail, refer now to the following description in conjunction with the accompanying Figures.

In one embodiment, a wireless sensor device is attached to a user and continuously and automatically obtains varying types of data including but not limited to ECG samples of the user. An application embedded within a processor of the wireless sensor device analyzes and compares the ECG samples to measure the user's heart function measurements.

FIG. 1 illustrates a wireless sensor device 100 in accordance with an embodiment. The wireless sensor device 100 includes a sensor 102, a processor 104 coupled to the sensor 102, a memory 106 coupled to the processor 104, an application 108 coupled to the memory 106, and a transmitter 110 coupled to the application 108. The sensor 102 obtains data from the user and transmits the data to the memory 106 and in turn to the application 108. The processor 104 executes the application 108 to measure R-R interval information of the user. The information is either used locally by the application to further derive other useful information, including but not limited to heart rate and respiratory rate, or is transmitted to the transmitter 110 and in turn relayed to another user or device.

In one embodiment, the sensor 102 comprises two electrodes and the processor 104 is a microprocessor. One of ordinary skill in the art readily recognizes that a variety of devices can be utilized for the processor 104, the memory 106, the application 108, and the transmitter 110 and that would be within the spirit and scope of the present invention.

Figure 2:
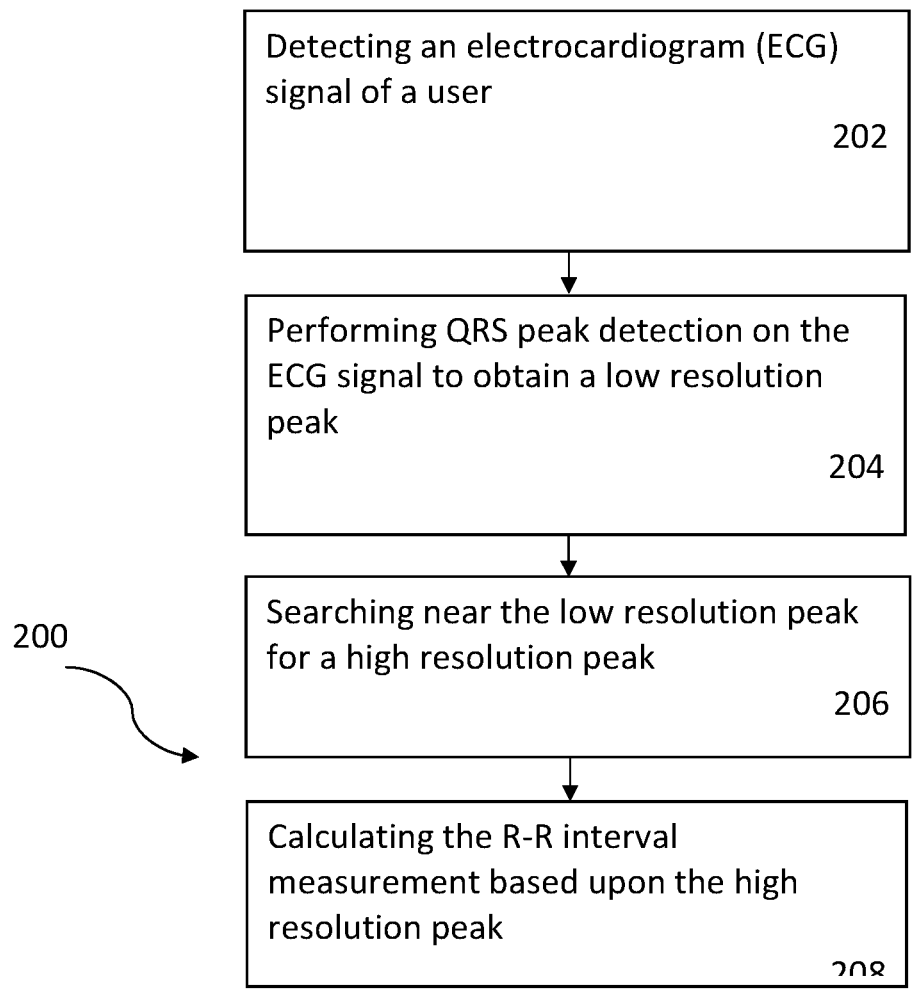
FIG. 2 illustrates a flow chart of a method in accordance with an embodiment.

FIG. 2 illustrates a flow chart of a method 200 in accordance with an embodiment. Referring to FIGS. 1 and 2 together, the method 200 comprises the wireless sensor device 100 detecting an electrocardiogram (ECG) signal of the user, via step 202. The method includes performing QRS peak detection on the ECG signal to obtain a low resolution peak, via step 204, and searching near the low resolution peak for a high resolution peak, via step 206. The R-R interval measurement of the user is calculated based upon the high resolution peak, via step 208. In this embodiment, the sensor 102 that is housed within the wireless sensor device 100 measures the ECG signal of the user. In another embodiment, notification information of the R-R interval measurement of the user is relayed by the wireless sensor device 100 to another user or device.

Figure 3:
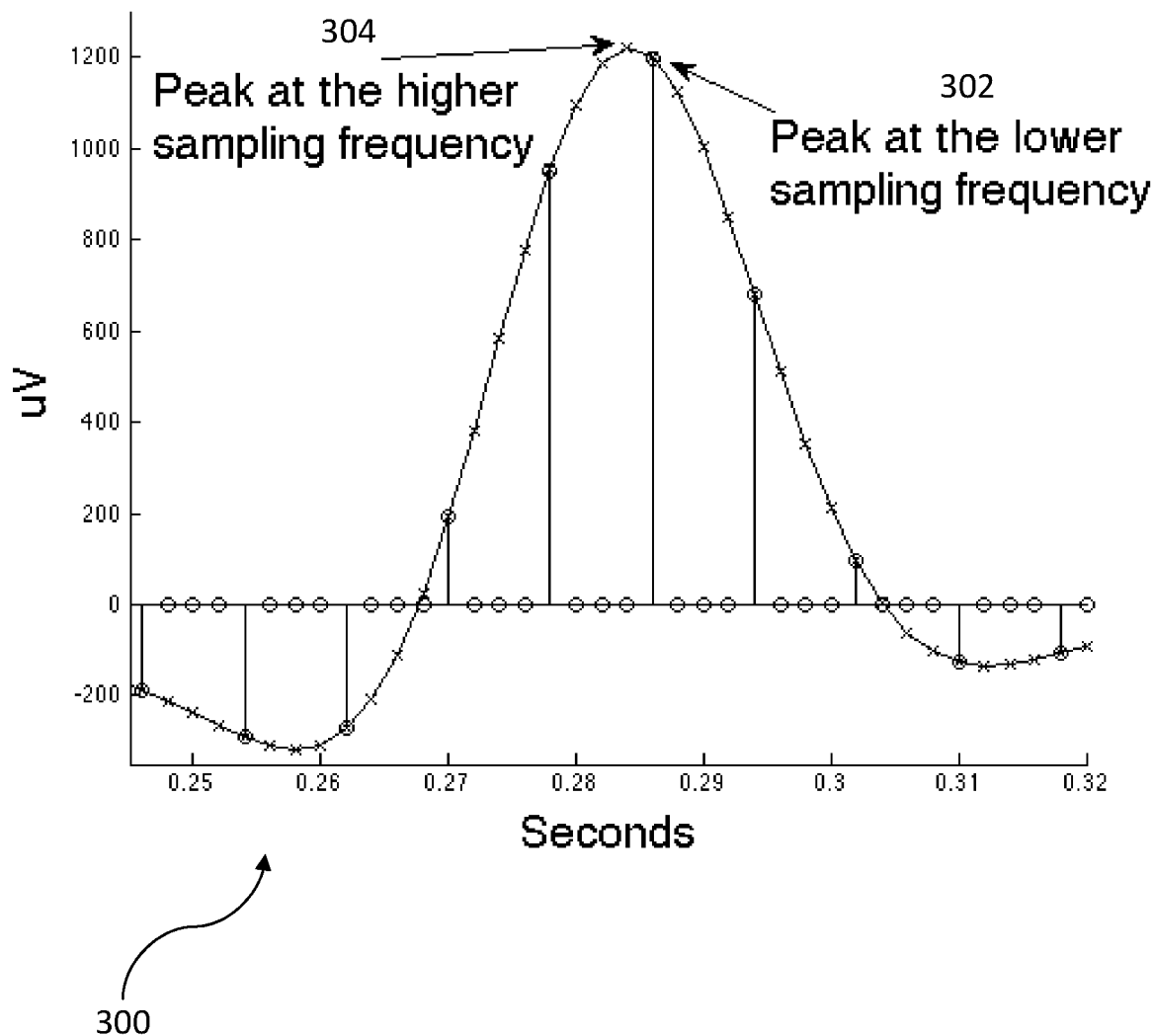
FIG. 3 illustrates a diagram of peak detection in accordance with an embodiment.

In one embodiment, after the wireless sensor device 100 detects the ECG signal of the user, a high fidelity digital ECG signal is acquired either by using an adequately high sampling rate or by re-sampling the signal in the digital domain or by both methodologies. In this embodiment, QRS peak detection is performed on a plurality of ECG samples of the ECG signal to obtain a QRS peak at a lower sampling rate. After finding the QRS peak at the lower sampling rate, the wireless sensor device 100, at a higher sampling rate, searches for a high resolution peak among all ECG samples that neighbor the QRS peak at the lower sampling rate. FIG. 3 illustrates a diagram 300 of peak detection in accordance with an embodiment. In the diagram 300, a peak 302 is detected at a lower sampling frequency and a peak 304 is subsequently detected at a higher sampling frequency.

In one embodiment, the wireless sensor device 100 samples an analog ECG signal at 500 Hz and feeds the analog ECG signal into an ADC. After conversion, the digital ECG signal is band-pass filtered and all of the ECG samples of the digital ECG signal are processed by a robust DSP algorithm for peak detection at 500 samples per second to output a high resolution peak. In this embodiment, the output of the robust DSP algorithm for peak detection is utilized for R-R interval calculation.

Figure 4:
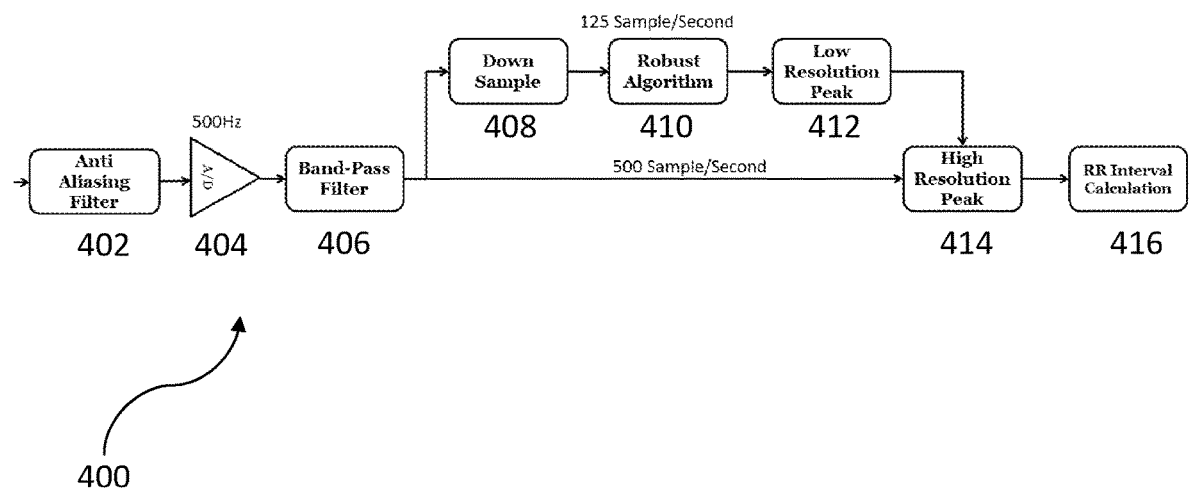
FIG. 4 illustrates a more detailed flow chart of a method in accordance with an embodiment.

FIG. 4 illustrates a more detailed flow chart of a method 400 in accordance with an embodiment. The method 400 detects a high resolution peak while utilizing lowered power consumption by sampling an analog ECG signal of a user at a higher sampling rate than is utilized by a robust DSP algorithm for peak detection. In one embodiment, the analog ECG signal is sampled at 500 samples per second (500 Hz) and the robust DSP algorithm utilizes 125 samples per second (125 Hz) for its computation.

In the method 400, a wireless sensor device detects an analog ECG signal of a user at a higher sampling rate. In one embodiment, the analog ECG signal is sampled at 500 Hz. The analog ECG signal is filtered with an anti-aliasing filter, via step 402, converted into a digital ECG signal by an ADC, via step 404, and filtered again with a band-pass filter, via step 406. After band-pass filtering, the digital ECG signal is down-sampled, via step 408, and processed at a lower sampling rate by the robust DSP algorithm, via step 410, to detect a low resolution peak 412. Thus, a subset of ECG samples of the digital ECG signal is processed by the robust DSP algorithm. In one embodiment, the subset comprises every fourth ECG sample of the digital ECG signal or 125 samples per second (125 Hz).

A high resolution peak is determined at the original higher sampling rate by a search over a span of points to the left and to the right of the detected low resolution peak 412, via step 414. In one embodiment, the span of points is from 3 points to the left to 3 points to the right of the detected low resolution peak 412. The determined high resolution peak is utilized in combination with a previously and/or subsequently determined high resolution peak to calculate an R-R interval, via step 416.

Figure 5:
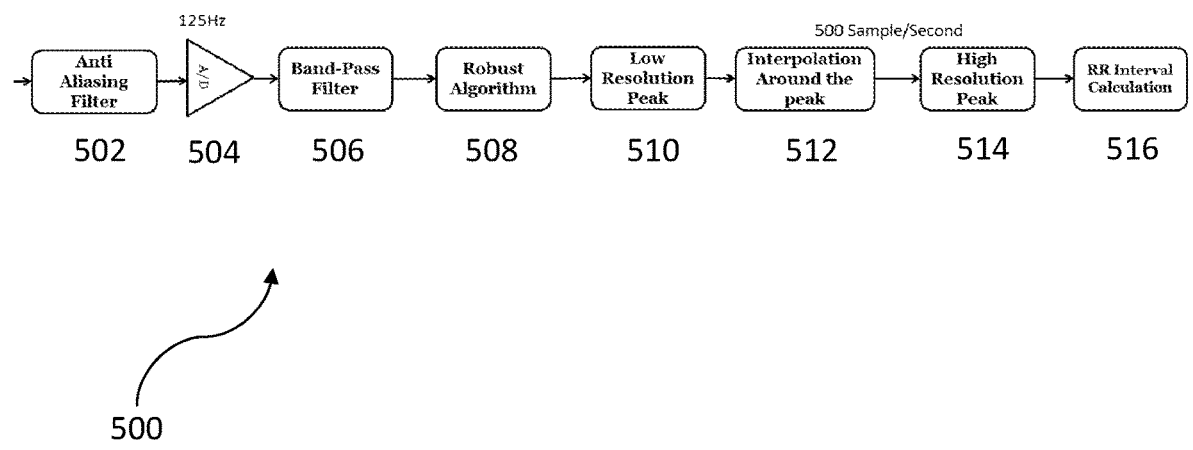
FIG. 5 illustrates a more detailed flow chart of a method in accordance with an embodiment.

FIG. 5 illustrates a more detailed flow chart of a method 500 in accordance with an embodiment. The method 500 detects a high resolution peak while utilizing lowered power consumption by sampling an analog ECG signal of a user at a lower sampling rate and re-sampling a digital ECG signal around a low resolution peak that has been detected by a robust DSP algorithm for peak detection. In one embodiment, the analog ECG signal is sampled at 125 samples per second (125 Hz).

In the method 500, a wireless sensor device detects an analog ECG signal of a user at a lower sampling rate. In one embodiment, the analog ECG signal is sampled at 125 Hz. The analog ECG signal is filtered with an anti-aliasing filter, via step 502, converted into a digital ECG signal by an ADC, via step 504, and filtered again with a band-pass filter, via step 506. After band-pass filtering, the robust DSP algorithm processes the digital ECG signal, via step 508, to detect a low resolution peak 510.

A high resolution peak is determined by choosing a span of points to the left and to the right of the detected low resolution peak 510 and by obtaining higher time resolution ECG samples by interpolating between these points, via step 512. In one embodiment, the span of points is from 10 points to the left to 10 points to the right of the detected low resolution peak 510.

After interpolation, the wireless sensor device searches for the high resolution peak at a higher time resolution over a span of points to the left and to the right of the previously detected peak among the interpolated ECG samples, via step 514. In one embodiment, the span of points is from 3 points to the left to 3 points to the right of the previously detected peak among the interpolated ECG samples. The determined high resolution peak is utilized in combination with a previously and/or subsequently determined high resolution peak to calculate an R-R interval, via step 516.

Figure 6:
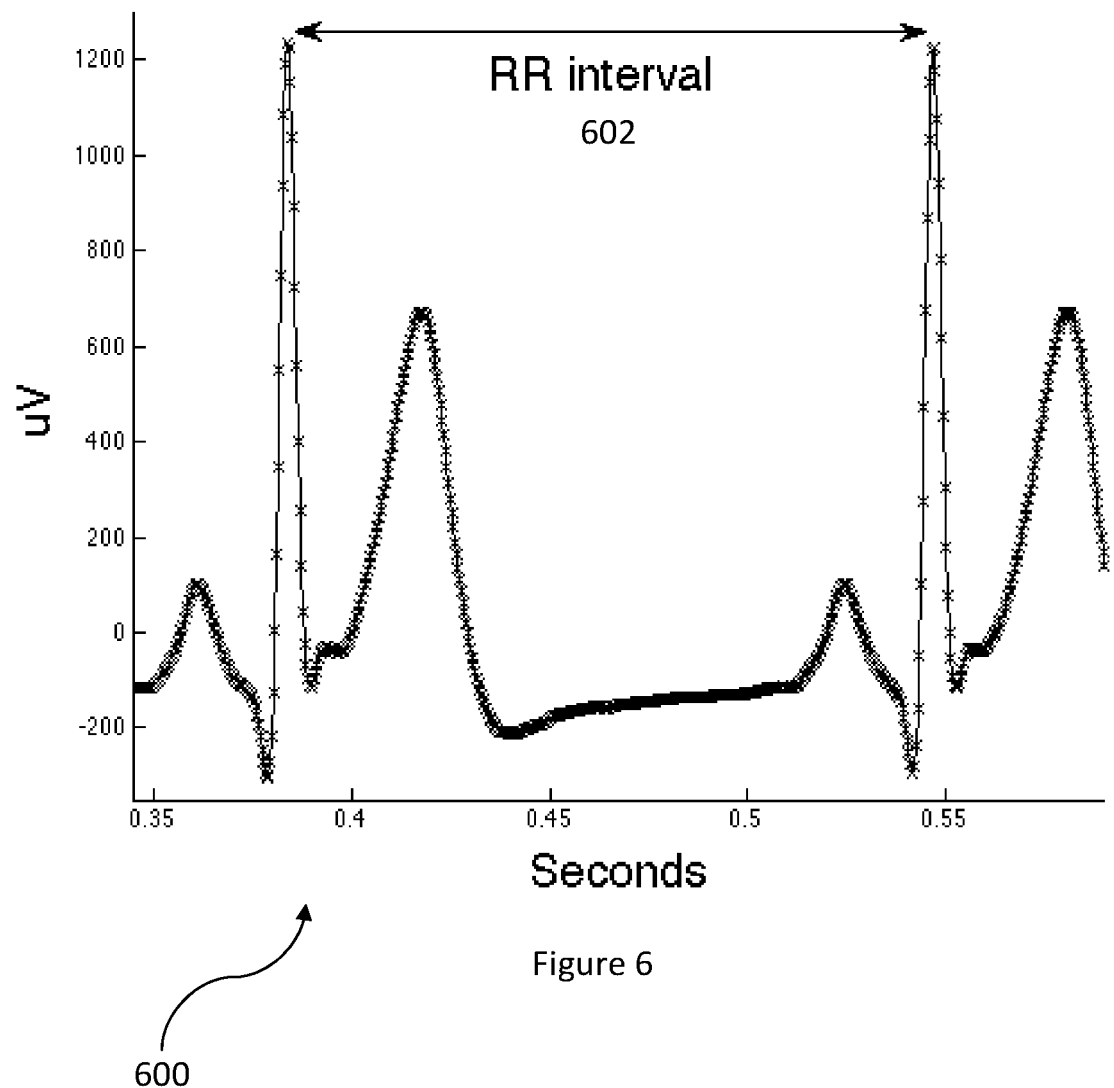
FIG. 6 illustrates a diagram of R-R interval in accordance with an embodiment.

The approaches described by FIG. 4 and FIG. 5 reduce the power consumption requirements of the wireless sensor device 100. The first approach of FIG. 4 offers a power reduction by utilizing a lower processing power. The second approach of FIG. 5 offers a power reduction by utilizing a lower analog power (lower sampling rate) and a lower processing power (computing R-R intervals less frequently). Both approaches output an R-R interval calculation that is utilized by the wireless sensor device 100 to compute the heart function measurements of the user. FIG. 6 illustrates a diagram 600 of R-R interval in accordance with an embodiment. In the diagram 600, an R-R interval 602 is denoted between a first and a second QRS peak.

As above described, the method and system allow for R-R interval measurement of a user based upon multi-rate ECG processing. By implementing at least one electrode within a wireless sensor device to detect an ECG signal and by acquiring a high fidelity digital ECG signal either by using an adequately high sampling rate or be re-sampling the signal in the digital domain or both, a power efficient R-R interval measurement system is achieved that decreases the power consumption usage of the wireless sensor device.

A method and system for R-R interval measurement of a user have been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to perform the functions described herein.

Furthermore, embodiments may take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for R-R interval measurement of a user using a wireless sensor device, the method comprising:
   detecting an electrocardiogram (ECG) signal of the user;
   performing QRS peak detection on the ECG signal to obtain a low resolution peak;
   searching proximate the low resolution peak for a high resolution peak by scanning a range of ECG sample points that span to the left and to the right of the low resolution peak; and
   calculating the R-R interval measurement based upon the high resolution peak.

2. The method of claim 1, wherein the detecting is at a high sampling rate, further comprising:
   filtering the ECG signal using an anti-aliasing filter;
   converting the ECG signal from an analog domain to a digital domain using an analog-to-digital converter (ADC);
   filtering the digital ECG signal using a band-pass filter;
   down-sampling the digital ECG signal at a low sampling rate;
   processing at least one ECG sample of the digital ECG signal using a digital signal processing (DSP) algorithm to detect a peak of the down-sampled ECG signal; and
   searching near the peak of the down-sampled ECG signal at the high sampling rate for the high resolution peak.

3. The method of claim 2, wherein the processing further comprises:
   processing every fourth ECG sample of the digital ECG signal using a robust digital signal processing (DSP) algorithm to detect a peak of the down-sampled ECG signal.

4. The method of claim 2, wherein the range of ECG sample points spans from 3 points to the left to 3 points to the right of the low resolution peak.

5. The method of claim 1, wherein the detecting is at a low sampling rate, further comprising:
   filtering the ECG signal using an anti-aliasing filter;
   converting the ECG signal from an analog domain to a digital domain using an analog-to-digital converter (ADC);
   filtering the digital ECG signal using a band-pass filter;
   processing the digital ECG signal using a digital signal processing (DSP) algorithm to detect the low resolution peak; and
   searching near the low resolution peak for the high resolution peak.

6. The method of claim 5, wherein the searching further comprises:
   interpolating between the range to obtain high resolution interpolated samples; and
   searching within the high resolution interpolated samples to determine the high resolution peak.

7. The method of claim 6, wherein the range of ECG sample points spans from 10 points to the left to 10 points to the right of the low resolution peak and wherein the searching within spans from 3 points to the left to 3 points to the right of the high resolution interpolated samples.

8. The method of claim 1, wherein the calculating further comprises:
comparing the high resolution peak with another previously calculated high resolution peak to compute the R-R interval calculation.

9. The method of claim 1, further comprising:
attaching a wireless sensor device to the user via at least one electrode; and
detecting the ECG signal of the user by the wireless sensor device.

10. The method of claim 1, wherein the low resolution peak is a QRS peak at a lower sampling rate of 125 Hz.

11. The method of claim 1, wherein the high resolution peak is a QRS peak at a higher sampling rate of 500 Hz.

* * * * *